US011065386B2

(12) United States Patent
Atterbury et al.

(10) Patent No.: US 11,065,386 B2
(45) Date of Patent: Jul. 20, 2021

(54) AUTOMATIC MEDICATION INJECTION DEVICE WITH AUDIBLE INDICATION OF INJECTING PROGRESS

(71) Applicant: Eli Lilly and Company, Indianapolis, IN (US)

(72) Inventors: William G. Atterbury, Columbus, OH (US); Steven Michael Madland, Columbus, OH (US); Christopher Paul McKenzie, Lancaster, OH (US); Jessica Diane Modlich, Columbus, OH (US)

(73) Assignee: Eli Lilly and Company, Indianapolis, IN (US)

( * ) Notice: Subject to any disclaimer, the term of this patent is extended or adjusted under 35 U.S.C. 154(b) by 869 days.

(21) Appl. No.: 15/527,022

(22) PCT Filed: Dec. 1, 2015

(86) PCT No.: PCT/US2015/063190
§ 371 (c)(1),
(2) Date: May 16, 2017

(87) PCT Pub. No.: WO2016/089871
PCT Pub. Date: Jun. 19, 2016

(65) Prior Publication Data
US 2017/0354779 A1 Dec. 14, 2017

Related U.S. Application Data

(60) Provisional application No. 62/086,929, filed on Dec. 3, 2014.

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/2455* (2013.01); *A61M 5/3157* (2013.01);
(Continued)

(58) Field of Classification Search
CPC ............ A61M 5/2033; A61M 5/31568; A61M 5/2455; A61M 5/31511; A61M 5/3157;
(Continued)

(56) References Cited

U.S. PATENT DOCUMENTS 4,466,426 A * 8/1984 Blackman ........... A61M 5/3158
600/5
5,582,598 A 12/1996 Chanoch
(Continued)

FOREIGN PATENT DOCUMENTS

CA 2231868 3/1997
EP 0496141 4/1997
(Continued)

OTHER PUBLICATIONS

Patent Cooperation Treaty International Search Report and Written Opinion of the International Searching Authority pertaining to International Application No. PCT/US2015/063190; dated Feb. 12, 2016.
(Continued)

*Primary Examiner* — Nathan R Price
*Assistant Examiner* — John A Doubrava
(74) *Attorney, Agent, or Firm* — M. Daniel Spillman

(57) ABSTRACT

An automatic medication injection device that provides a user with audible notice of injecting progress. The device in one form includes a plurality of sound elements located on drive mechanism portion that inserts within a barrel of a container of medication to advance a sealing plunger of that container. The device also includes at least one actuating element movable axially with the container of medication
(Continued)

within the device housing, which at least one actuating element arranged to engage the plurality of sound elements to generate audible notices as the advancing portion moves past the at least one actuating element when advancing the sealing plunger for an injection.

30 Claims, 10 Drawing Sheets

(51) Int. Cl.
*A61M 5/315* (2006.01)
*A61M 5/32* (2006.01)

(52) U.S. Cl.
CPC .... *A61M 5/31511* (2013.01); *A61M 5/31568* (2013.01); *A61M 5/31566* (2013.01); *A61M 5/326* (2013.01); *A61M 2005/206* (2013.01); *A61M 2205/581* (2013.01)

(58) Field of Classification Search
CPC ........ A61M 2205/58; A61M 2205/582; A61M 2205/581
See application file for complete search history.

(56) References Cited

U.S. PATENT DOCUMENTS

| | | |
|---|---|---|
| 5,674,204 A | 10/1997 | Chanoch |
| 5,688,251 A | 11/1997 | Chanoch |
| 5,725,508 A | 3/1998 | Chanoch et al. |
| 5,807,346 A | 9/1998 | Frezza |
| 5,827,232 A | 10/1998 | Chanoch et al. |
| 7,611,495 B1 | 11/2009 | Gianturco |
| 7,678,084 B2 | 3/2010 | Judson et al. |
| 7,758,550 B2 | 7/2010 | Bollenbach et al. |
| 7,976,499 B2 | 7/2011 | Grunhut et al. |
| 8,038,655 B2 | 10/2011 | Burren et al. |
| 8,075,517 B2 | 12/2011 | Karlsson et al. |
| 9,872,961 B2 | 1/2018 | Fourt et al. |
| 2007/0265579 A1* | 11/2007 | Kleyman ................. A61C 5/62 604/207 |
| 2008/0077094 A1 | 3/2008 | Burren et al. |
| 2009/0060924 A1* | 3/2009 | Korytko ................. C07K 16/22 424/172.1 |
| 2010/0022751 A1* | 1/2010 | Shone ..................... C07K 14/33 530/350 |
| 2010/0049125 A1* | 2/2010 | James .................. A61M 5/2033 604/110 |
| 2010/0094207 A1 | 4/2010 | Boyd et al. |
| 2010/0137798 A1 | 6/2010 | Streit et al. |
| 2010/0168072 A1* | 7/2010 | Wynne ................. A61K 31/416 514/171 |
| 2011/0092915 A1 | 4/2011 | Olson et al. |
| 2012/0172811 A1* | 7/2012 | Enggaard ................ A61M 5/20 604/193 |
| 2013/0197449 A1 | 8/2013 | Franklin |
| 2013/0211330 A1 | 8/2013 | Pedersen et al. |
| 2013/0296308 A1* | 11/2013 | Brodney ............. C07D 513/04 514/224.2 |
| 2014/0243749 A1* | 8/2014 | Edwards ................. A61M 15/08 604/187 |
| 2014/0314837 A1* | 10/2014 | Pfeifer ................... C07K 16/18 424/450 |
| 2015/0374919 A1* | 12/2015 | Gibson ............... A61M 5/3297 604/205 |

FOREIGN PATENT DOCUMENTS

| | | |
|---|---|---|
| EP | 2275159 | 1/2011 |
| JP | H04256758 | 9/1992 |
| WO | 2007132353 | 11/2007 |
| WO | 2008016381 | 2/2008 |
| WO | 2008083875 | 7/2008 |
| WO | 2009092807 | 7/2009 |
| WO | 2011003980 | 1/2011 |
| WO | 2013034984 | 3/2013 |
| WO | 2013057033 | 4/2013 |
| WO | 2014001319 | 1/2014 |
| WO | 2014165868 | 10/2014 |

OTHER PUBLICATIONS

PLEGRIDY™ Pen Instructions for Use, Issued Aug. 2014; Manufactured by Biogen Idec Inc.

* cited by examiner

AUTOMATIC MEDICATION INJECTION DEVICE WITH AUDIBLE INDICATION OF INJECTING PROGRESS

BACKGROUND OF THE INVENTION

The present invention pertains to medication injection devices, and, in particular, to medication injection devices having features that provide to the users of such devices audible information as to use.

Patients suffering from a number of different diseases frequently must inject themselves with medications. A variety of devices have been proposed to facilitate these injections. One type of device is a medication pen that may be adjusted manually to set a dose for delivery, and then operated manually to inject the set dose. This type of device may include clicker features that provide an audible clicking sound during dose injecting, as well as dose setting, for each unit of medication being injected, or being set for injection, respectively. The clicking sound that is produced during dose injecting may be useful for the user to understand how an injection is progressing.

Another type of device is an automatic medication injection device. This type of device typically includes a trigger that when operated by a user causes the device to automatically insert into the user a needle of a syringe that prior to triggering was disposed within the device housing, and then the device automatically injects a dose of medication through that inserted needle. In some cases, an automatic injection device does not so insert the needle into the user, but does, when triggered, automatically inject a dose of medication through the needle that has been manually inserted by the user. In a device of this type, the user does not completely control the speed of the injection as such is a function of the design of the device.

One potential shortcoming with using automatic injection devices relates to the fact that some users may be unsure they are using the devices correctly. Without some sort of feedback from the device when it is being used, a user may question whether an injection has commenced or whether it is finished. Uncertainty in the user about an injection progressing is particularly likely in cases where the injection takes a relatively long time to complete, possibly such as due to a large volume dose or a high viscosity dose of medication being delivered.

Automatic medication injection devices are known which produce audible clicks as the injection is in progress, or which produce clicks when the end of an injection is approaching. Some automatic medication injection device produces an audible click when an injection is complete so that the user knows the device can be removed from the injection site. Another known automatic medication injection device known as the Auvi-Q™ epinephrine injection includes recorded messages, and when the device is activated provides audible instructions or explanation that leads a user to operate the device properly, including a countdown and a message when the injection is complete.

Unfortunately, these types of audible indicators in automatic medication injection devices are not acceptable in all circumstances, for example such as when a less expensive device is required for a given application, or when further information about dosing status is desired from a non-electronic device, or when a user may think that a click stoppage means the device has stopped working as opposed to an injection being complete.

Thus, it would be desirable to provide an automatic medication injection device with an audible indicator which can overcome one or more of these and other shortcomings of the prior art.

BRIEF SUMMARY OF THE INVENTION

In one form thereof, the present invention provides an automatic medication injection device including a user grippable housing having a length extending in an axial direction between a proximal end and a distal end, a container of medication including an outlet that is disposed proximally of the housing proximal end at least during injection, the container including a barrel and a sealing plunger, the sealing plunger in sealing engagement with the barrel, a drive mechanism within the housing which when triggered automatically advances the container of medication within the housing and advances the sealing plunger proximally within the container to force medication from the outlet, the drive mechanism including an advancing portion that inserts within the barrel, a plurality of sound elements located on the advancing portion, and at least one actuating element movable axially within the housing with the container of medication, the at least one actuating element arranged to engage the plurality of sound elements to generate audible notices as the advancing portion moves past the at least one actuating element when advancing the sealing plunger for an injection.

In another form thereof, the present invention provides an automatic medication injection device including a user grippable housing having a length extending in an axial direction between a proximal end and a distal end, a container of medication including an outlet that is disposed proximally of the housing proximal end at least during injection, a drive mechanism within the housing which when triggered automatically advances to force medication from the outlet for an injection, a plurality of sound elements within the housing, at least one actuating element within the housing, at least one of the at least one actuating element and the plurality of sound elements configured to travel within the housing when the drive mechanism advances to force medication from the outlet so that the plurality of sound elements and the at least one actuating element move relative to each other to have the at least one actuating element engage the plurality of sound elements to generate audible notices during the injection. Each of the plurality of sound elements other than a most distal sound element has a spacing in the axial direction from a proximally adjacent one of the sound elements. The spacings are selected to provide a pattern of shortening time intervals between the audible notices throughout at least a portion of time that the drive mechanism advances to force medication from the outlet.

One advantage of the present invention is that an automatic medication injection device may be provided with an audible indicator that has a changing cadence to indicate the approaching of an end of dose.

Still another advantage of the present invention is that an automatic medication injection device may be provided with an audible indicator in a ready fashion with limited parts modifications.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
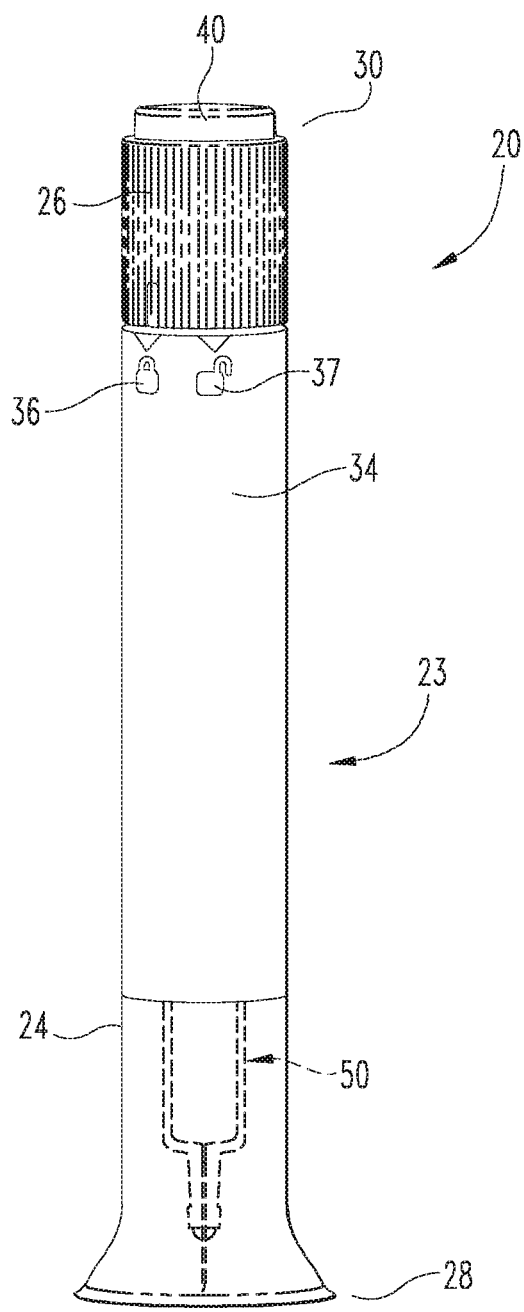
FIG. 1 is a front view of an automatic injection device with an audible injecting progress indicator shown prior to use.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
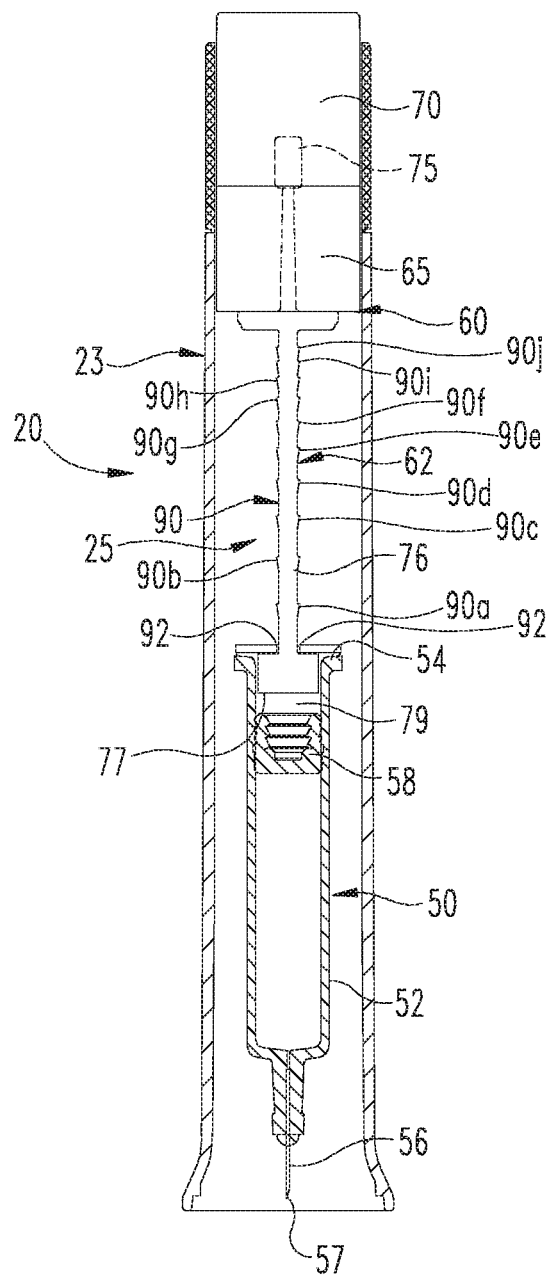
FIG. 2 is a cross-sectional side view of the device of FIG. 1 prior to use, wherein portions of the device are omitted or shown schematically.
Figure 3:
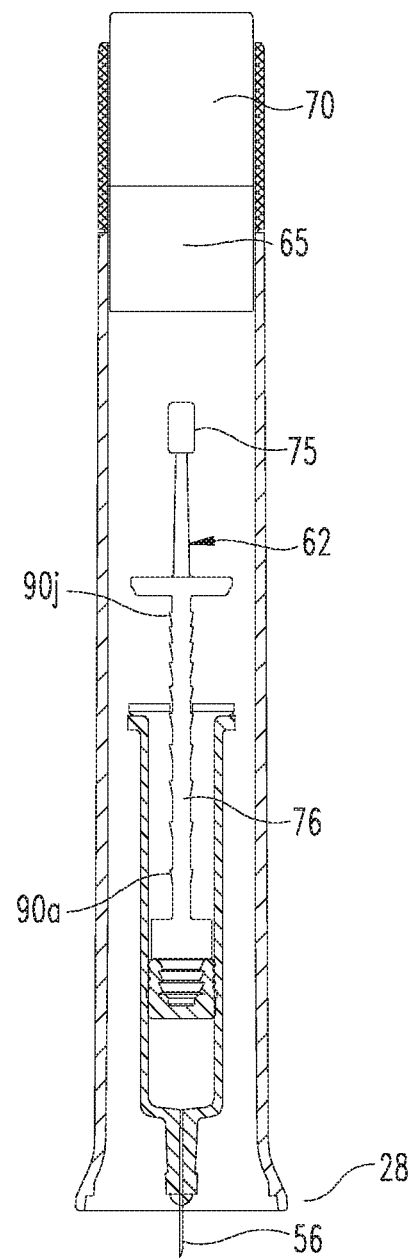
FIG. 3 is a cross-sectional side view of the device of FIG. 2 after triggering and at a point when the device needle has been extended for user penetration and the medication dose is in the process of being injected through that needle.

Referring now to FIGS. 1, 2 and 3, there are shown different views of a first embodiment of an automatic medication injection device with an audible injecting progress indicator of the present invention. The automatic medication injection device, generally designated 20, is shown and described as a device that when its trigger is manually operated, its needled syringe 50 is automatically driven downward such that its injection needle projects beyond the bottom end of the device housing to penetrate the user. The device then proceeds to inject automatically, that is without further user action, the entire medication contents of the device through the injection needle.

The audible indicator, generally indicated at 25, find beneficial application in the device 20 described herein, but such application is merely illustrative and not intended to be limiting. The audible indicator can be used in many different types of automatic medication injection devices where its benefits are desired, including devices in which the insertion of the needle is manually performed but the forcing of the medicine through such needle is automatic once triggered.

It will be appreciated from the following description that device 20 is conceptually similar in various aspects to the devices disclosed in International Publication Number WO 2014/062488, which publication is incorporated herein by reference in its entirety.

Device 20 includes an outer housing 23, which is grippable by a user and in which are operationally disposed working components of the device. The outer housing 23 includes a safety sleeve 26 and a main body 24 that together form the height of the outer housing extending in the axial direction between proximal end 28 and distal end 30. The main body 24 is shown formed of a transparent plastic, and an opaque wrap or label 34 around the upper portion of the main body 24 hides working device components protectively encased within the housing. Label 34 may include information, such as icons 36 associated with locking, or product details or instructions for use. Safety sleeve 26 is rotatable by the user relative to main body 24 between locked and unlocked conditions as indicated at icons 36, 37. A button 40 that is part of the trigger assembly protrudes in the axial direction from the top or distal end 30 of the housing. When properly rotationally oriented by rotation of sleeve 26, button 40 is unlocked such that it can be depressed in the proximal direction to start the automatic injection function of device 20. As used herein, distal and proximal refer to axial locations relative to an injection site when the device is oriented for use at such site, whereby, for example, proximal end of the housing refers to the housing end that is closest to such injection site. The shown triggering button 40 is the manner in which device 20 is triggered, but other triggering designs are known and can be used in devices with audible injecting progress indicators. A needle cap that is typically provided on device 20 and then removed prior to use is not shown in the Figures.

As further shown abstractly in FIG. 2, device 20 includes a medication-filled container provided in the form of a syringe, generally designated 50, that is axially movable within the housing 23. Syringe 50 is of a conventional design and includes a transparent barrel 52 with a flange 54 at its distal end, an injection needle 56 that serves as an outlet for the barrel 52, and a sealing plunger 58. Injection needle 56 is mounted at the proximal end of barrel 52 and in fluid communication with the medication contents of the barrel. Sealing plunger 58 is an elastomeric sealing member having an outer radial periphery adapted to slidably and sealingly engage the inner circumference or inner radial periphery of the barrel 52 so as to seal medication within the barrel below the proximal face of the sealing plunger 58.

Syringe 50 is disposed completely within the housing main body 24 prior to use near the proximal end 28 and is visible in part from the exterior through the housing 23 below label 34. Prior to device 20 being used for an injection, and as shown in FIGS. 1 and 2, the syringe 50 is positioned such that the tip 57 of its needle 56 is recessed within the housing 23. During an injection as shown in FIG. 3, the proximal tip 57 is shifted proximally of the housing proximal end 28 for penetrating the user.

Device 20 may use a conventional mechanical drive mechanism to move the syringe 50 from the retracted position shown in FIGS. 1 and 2 to the injecting position shown in FIG. 3, and then to advance the sealing plunger 58 proximally within barrel 52 to force the medication through the outlet tip 57 of needle 56. The particulars of the drive mechanism described below are not material to the shown embodiment of the invention, other than that it includes a member that moves within housing 23 when the drive mechanism advances sealing plunger 58 and on which the sound elements of audible indicator 25 are located, as the audible indicator can be adapted for use with different such mechanisms.

The drive mechanism of device 20 is abstractly shown in FIG. 2 at 60 as including an axially extending plunger element 62, a driver 65, and a trigger assembly 70 that includes button 40. Plunger element 62 has an upper or distal end diagrammatically shown at 75 in FIGS. 2 and 3 that is cooperatively designed with the trigger assembly 70 to be axially retained by the trigger assembly 70 until release by the depressing of button 40. When the plunger element 62 is so released the driver 65, which may be a compression spring already under load, forces the plunger element 62 proximally. When element 62 is so moved, the elongated drive portion 76 of plunger element 62 which fits within the container barrel 52 moves to have its proximal end 77 first close the shown gap 79, and then abuts the sealing element 58. Then, the continued driving of plunger element 62 proximally by driver 65 advances the sealing element 58 proximally relative to the housing 23 an identical amount. The movement of the plunger element 62 and sealing plunger 58 first shifts the entire syringe 50 to a needle inserted position shown in FIG. 3 at which further proximal movement of the syringe 50 within the housing is prevented. Further movement of plunger element 62 by driver 65, which in FIG. 3 is not shown in physical engagement with plunger element 62 but would be to continue delivering mechanical force thereto, then advances the sealing plunger 58 proximally within the barrel 52 to force medicine from the syringe through needle 56.

Other types of drive mechanisms, such as electromechanical or chemical reaction powered drive mechanisms that work when triggered to shift the plunger element 62 may be employed with an audible progress indicator 25.

The audible injecting progress indicator 25 is provided by a number of sound elements 90 that each interacts with an actuating element 92 to produce a sound when engaged. The engagement occurs when a sound element 90 and actuating element 92 experience a relative axial motion so as to move past each other during the time that medication is being forced through needle 56.

Sound elements 90 are shown in FIGS. 2 and 3 as being a series of ten ramp-shaped protrusions or sound elements 90a, 90b, 90c, 90d, 90e, 90f, 90g, 90h, 90i and 90j that are integrally formed with drive portion 76 of plunger element 62. The sound elements 90 could be provided on different portions of the drive mechanism, or an additional element which is moved by the drive mechanism during the injecting of medication. Each of ramp-shaped sound elements 90a-j is shaped identically to provide a same volume click. The axial spacing between adjacent protrusions 90a-j, as well as the total number of protrusions, are designed to achieve a desired sound pattern. Two identical sets of sound elements 90a-j are provided and are spaced 180 degrees apart around drive portion 76, and such a configuration is highly suitable where the drive portion 76 and the actuating element 92 are provided do not experience relative rotation during injecting. The use of aft two actuating elements 92 acting on opposite sides of drive portion 76, with each actuating element 92 engaging a different set of sound elements 90, provides balanced forces on the plunger element 62.

As few as one set of sound elements 90 with one actuating element 92 can be provided within the scope of the invention. Additional sets of identical sound elements 90 and actuating elements 92 alternatively may be provided. While ten sound elements are shown within each set, more or less sound elements could be used. Still further, rather than the sets of sound elements 90 on different sides or angular regions of the drive portion 76 being identical, the axial locations or spacing or shapes of the sound elements may be different on different sides so long as the sound elements, with their respective actuating arms, all together achieve the desired sound pattern during use. Still further, the sound elements alternatively could be placed on the syringe or housing and the actuating arms be provided on the plunger element.

Sound elements 90 are selectively positioned along the height of plunger element 62 during its design in view of the overall workings of device 20 to achieve a desired sound pattern. The sound elements 90a-j are axially spaced from each other to provide a desired pattern of time intervals between audible notices. The axial spacing can account for changing axial speeds of plunger element 62 as it travels to shift sealing plunger 58 downward into barrel 52 to force medication from syringe 50. The spacing, and provided the extent of the axial range of the sound elements is sufficient, allows a sequence of audible notices to be provided having a desired pattern of time intervals between audible notices throughout the forcing of medication from the container outlet. The changing speeds, which is due to factors such as fluid dynamics, air bubbles within a typical syringe, as well as the force profile of the drive mechanism 65, may be determined by empirical analysis of similar devices. In a device which has a drive mechanism that can advance the syringe plunger at a substantially constant speed throughout its travel, the sound elements 90 need not have variable spacing except as necessary to provide a change in cadence in audible notices to indicate an approaching end of injection if such is desired in that embodiment. Still further, and again in a device with a changing speed drive mechanism and in which a change in cadence in audible notices to indicate an approaching end of injection is desired, the sound elements 90 need not have variable spacing, except as necessary to provide an end of injection time dependent cadence, so long as the frequency of any sounds produced by the sound elements up until an end of injection pattern is desired can vary, such as slow down or speed up.

The positioning of the sound elements 90 along the height of plunger element 62 as shown in FIGS. 2 and 3 achieves an audible clicking feature that has a first click, associated with sound element 90a, when the syringe plunger 58 starts to move within barrel 52 to force medication through needle 57, and has a final click, associated with sound element 90j, when the drive mechanism 60 has completed, or nearly completed such as for the sake of design tolerances, its downward driving of plunger 58 within barrel 52. Different periods of clicking can be provided in alternate designs. While during their creation the clicks come at least one per second, slower click frequencies are also possible.

The shape of each of sound elements 90a-j is shown as a ramp that cams the actuating elements 92 radially outward such that when the actuating elements 92 pass over the sound elements 90a-j, the actuating elements 92 snap back radially inward into contact with syringe plunger 62, in particular the planar surface 93 forming the base of channel 91 or alternatively the start of the next sound element if such are so closely spaced together, to produce a single short and sharp sound referred to as a click. In alternate embodiments, differently shaped features, or the use of sequenced stick-slip materials, may be used to generate different sounds, such as similar to crickets chirping or fingernails on chalkboard. The design of the sound elements, as such elements need not serve another purposes such as a ratchet type backup preventing feature, may be dedicated to sound production.

The audible noises or signals produced by sound elements 90 and actuating elements 92 may be designed to produce a variety of different patterns, which patterns may involve the time intervals between successive sounds and/or the intensity of the sounds and/or the type of sounds. The embodiment shown in FIGS. 2 and 3 uses sound elements 90 to provide a clicking sound throughout the forcing of medication from syringe 50 by movement of plunger element 62, which clicking sounds, after the first sound associated with sound element 90$a$, has a constant time interval for the next three sounds produced by sound elements 90$b$, 90$c$ and 90$d$, followed by a steadily decreasing time interval for the remaining six sounds produced by sound elements 90$e$, 90$f$, 90$g$, 90$h$, 90$i$ and 90$j$. This speeding up of clicking sounds as the end of injection approaches is readily explainable to a user as the nearing of an end of a process. Rather than time intervals for the last six clicks shortening as described above, the shortening time intervals for fewer such last clicks, such as one, two, three, four of five could be employed in alternate embodiments. In addition, more than the last six clicks, including up to all of the clicks, could have a shortening time interval. Or, instead of a steadily decreasing time interval for the last several clicks, the time interval for these last clicks, such as two or three clicks, could be the same, but shorter than the earlier clicks, to indicate to the user a change in the process.

In still another embodiment, the axial spacing between the sound elements 90 could be used to account solely for changing speeds of the plunger element 62 in that the clicks from the sound elements would have a constant time interval or temporal spacing throughout their use.

Rather than the sounds of sound elements 90 being identical but for their temporal spacing, the sounds may be different near or at the end of injection to notify a user. For example, the last sounds produced could be of a different volume, for example a uniformly louder, or a crescendoing, volume. The last sounds produced also could be of a different type, such as cricket sounds that are noticeably different from clicking sounds at the start of the injection.

The actuating elements 92 are positioned within housing 23 to engage the sound elements 90 during the injection process. Two actuating arms 92, one on each of two opposite sides of plunger drive portion 76 in axial alignment with a set of sound elements 90$a$-$j$, are provided. As the sound elements 90$a$-$j$ axially pass between actuating elements 92, the actuating elements 92 are forced apart in the radial direction, and the actuating elements snapping back radially inward into contact with plunger element 62 when each of sound elements 90$a$-90$j$ pass produces the audible signal in this embodiment. Actuating elements 92 shown in FIGS. 2 and 3 moves with syringe 50 as the syringe is moved proximally. In an alternate embodiment, the actuating elements 92 could be attached to, or integrally formed with, the housing to be axially fixed relative thereto, but such would require the sound elements to span a shorter axial distance of the shown plunger element 62 if clicks during needle insertion were to be avoided.

Figure 4:
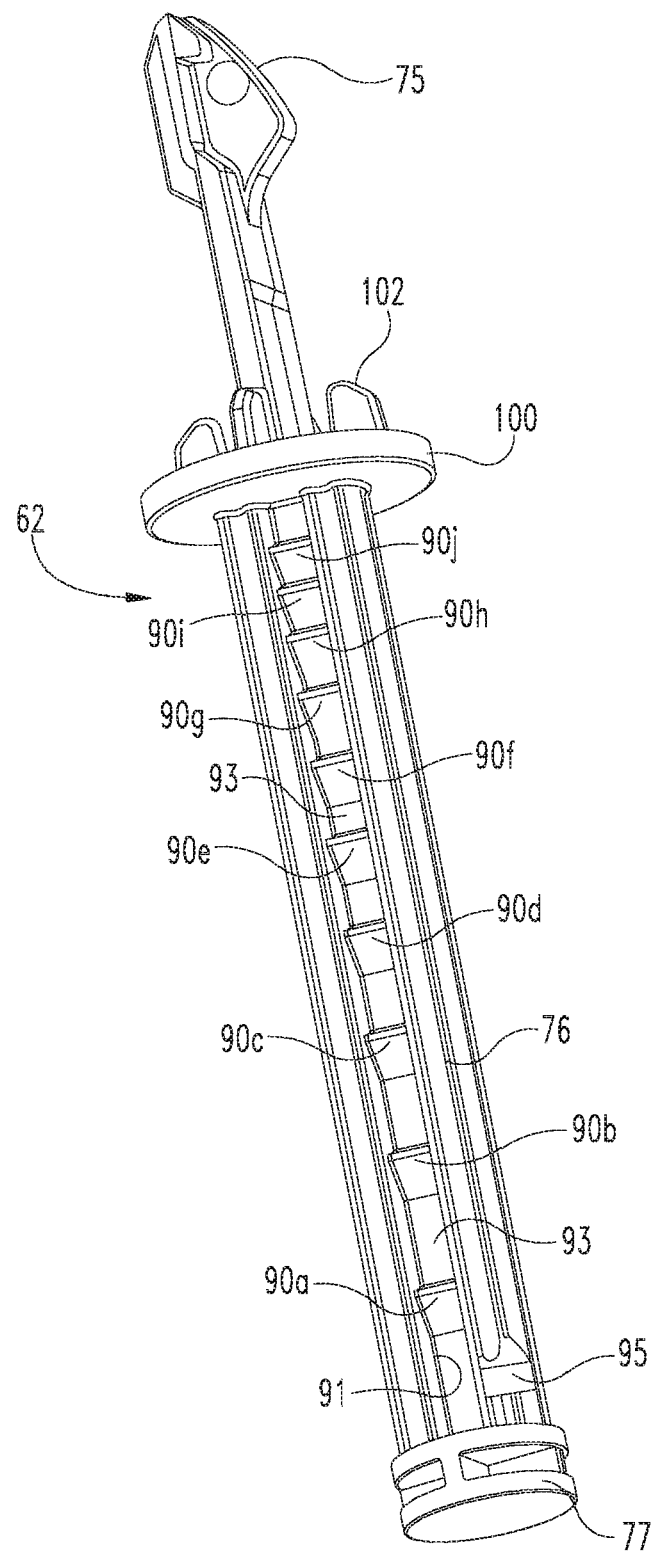
FIG. 4 is a perspective view of the sound elements of the audible indicator of FIG. 1, which sound elements are disposed on a plunger.
Figure 5:
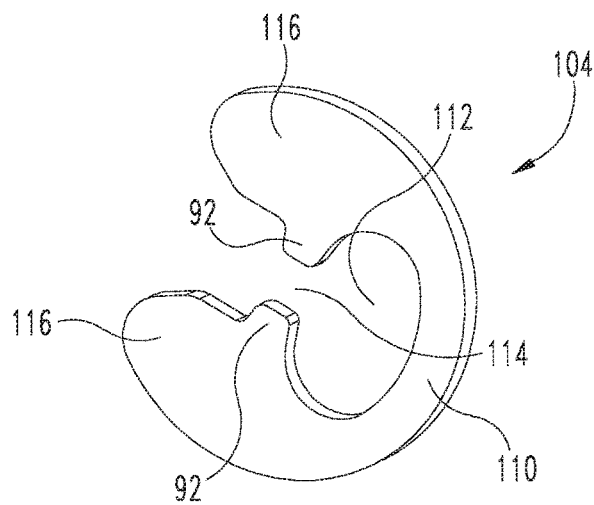
FIG. 5 is a perspective view of a clip with actuating element of the audible indicator of FIG. 1.
Figure 6:
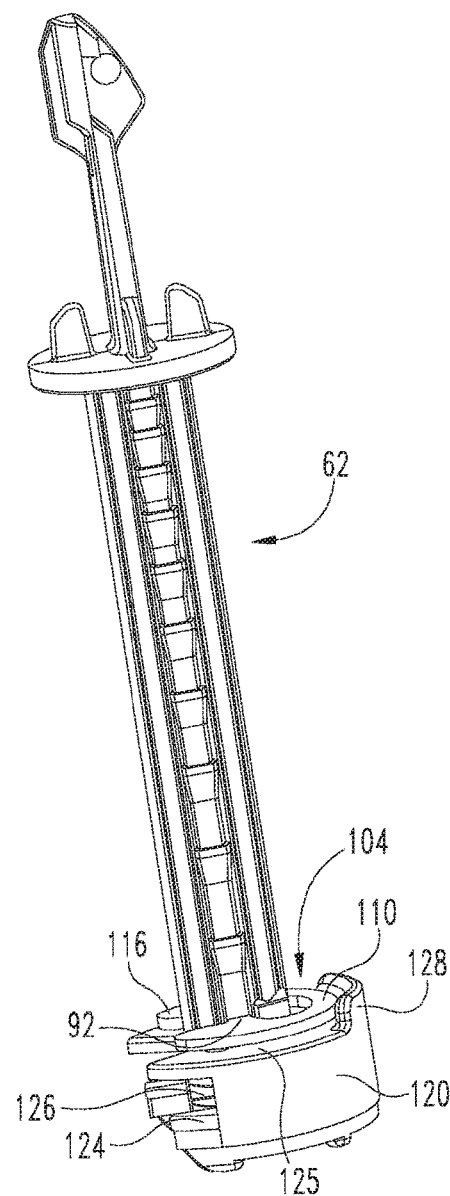
FIG. 6 is a perspective view of select portions of an automatic medication injection device which provides audible indications during injecting.

Referring now to FIGS. 4-6, there is further shown details of one suitable manner of providing the audible injecting progress indicator 25 of FIGS. 1-3. Plunger element 62 is shown alone in FIG. 4 and is formed in one piece out of a thermoplastic material capable of being injection molded, such as polyoxymethylene. The drive portion 76 is generally bar shape and terminates with a cylindrical, syringe sealing element-engaging foot at the proximal end 77. Drive portion 76 depends from an enlarged disc portion 100 the distal face of which is acted upon by a coil spring of driver 65. Dogs 102 for centering the driver spring upwardly project from disc portion 100 as does the trigger engaging prong 75.

Sound elements 90$a$-90$j$ are formed in axial alignment within a longitudinally extending channel 91 in drive portion 76. A notch 95 in drive portion 76 leads to channel 91. The not shown opposite side of drive portion 76 is similarly configured.

The actuating elements 92 are provided on a clip 104 shown alone in FIG. 5. Clip 104 is a plate-shaped member formed in one piece out of a lubricated polycarbonate having sufficient resiliency yet rigidity to provide its sound producing function. Clip 104 is formed with a curved, continuous spring beam 110 that has opposite angular ends from which extend in the inward direction two facing tabs that function as actuating arms 92. Actuating arms or tabs 92 are spaced from each other to define a gap 114 through which plunger drive portion 76 extends such that tabs 92 fit within channels 91 and sound elements 90$a$-90$j$ are engaged by the facing edges of tabs 92 as the elements pass thereby during use. Spring beam 110 allows tabs 92 to splay apart elastically to temporarily increase gap 114 when tabs 92 and the sound elements 90$a$-90$j$ are in contact. Gap 114 leads to a larger opening 112 defined by the interior of beam 110 which further accommodates drive portion 76 for free axial passage. Clip 104 can be installed flanking drive portion 76 by passing tabs 92 through notches 95.

Clip 104 also includes lobe-shaped counterweight portions 116 that extend from the ends of spring beam 110. Counterweight portions 116 add weight to increase the sound volume of the generated clicks. A louder sound may further be produced by configuring clip 104 to have a dynamic response of the torsional stiffness of beam 110, which relates to twisting of the clip around an axis perpendicular to the axis of the device, being the same as the dynamic response of the bending stiffness of beam 110, which relates to bending being within the plane of the clip, thereby causing the clip to respond in both torsional and bending simultaneously.

Clip 104 is disposed within device 20 distally of syringe 50 and so as to be axially movable with syringe 50 relative to housing 23. A manner of so providing this feature is by having clip 104 seated or rested on a part that holds the syringe. Referring now to FIG. 6, the plunger element 62 of FIG. 4 and the clip 104 of FIG. 5 are operationally assembled and shown with a syringe carriage 120 of device 20 that so holds syringe 50 (not shown).

Syringe carriage 120 includes a rigid base formed of a C-shaped lower region 124 and an apertured top region 125. The carriage defines a cavity 126 into which syringe flange 54 (not shown) can be inserted from the side during device assembly such that carriage 120 captures the flange 54 axially. Clip 104 seats on the top region 125, and ridge 128 aids in keeping clip 104 from laterally moving away from the syringe plunger element 76. The sound properties of audible injecting progress indicator 25 can be readily changed or tuned by the manufacturer by replacing clip 104 with a differently configured clip.

Figure 7:
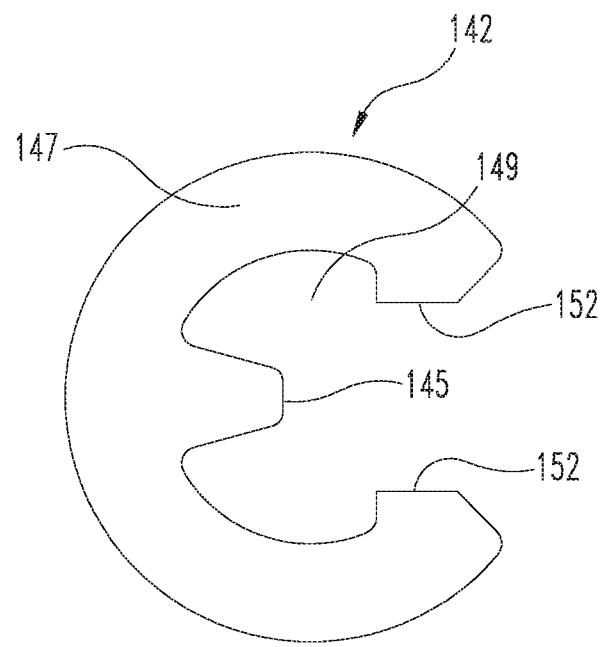
FIG. 7 is a top view of a clip with actuating element for an alternate audible indicator.
Figure 8:
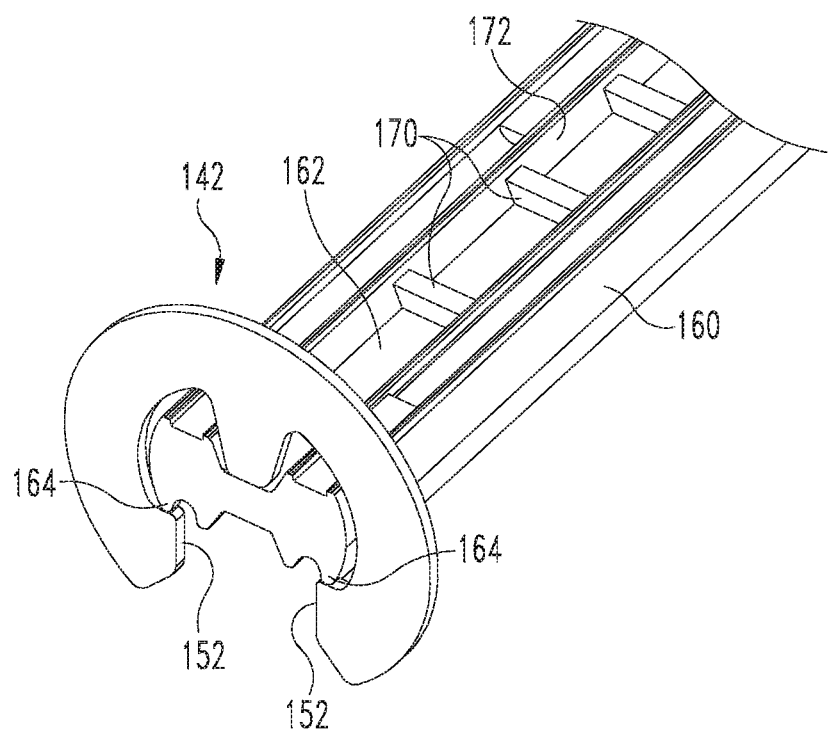
FIG. 8 is a perspective view of the clip of FIG. 7 mounted to a partially shown plunger element that includes sound elements.
Figure 9:
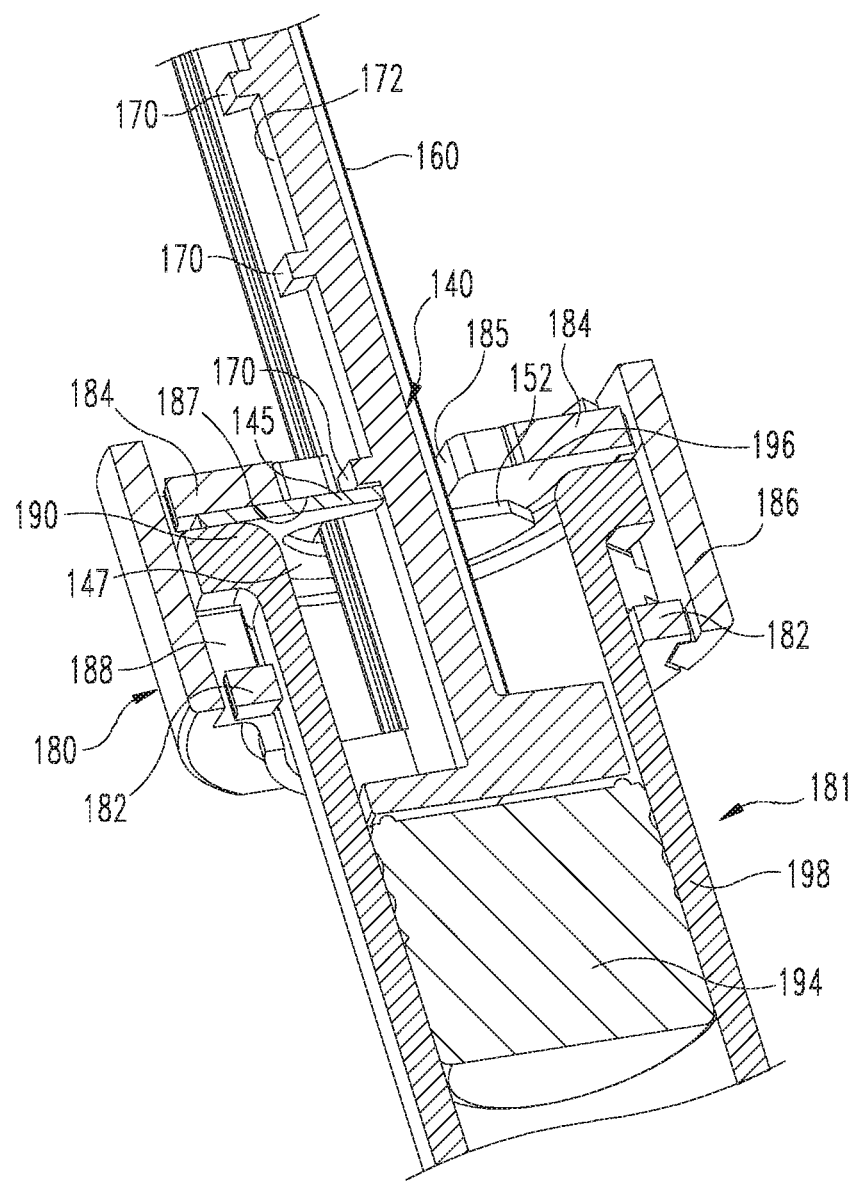
FIG. 9 is a perspective view in longitudinal cross-section of select portions of an automatic medication injection device which includes the actuating element and sound elements of FIGS. 7 and 8.

Referring now to FIGS. 7-9, there is shown details of an alternate audible injecting progress indicator generally designated 140. A single actuating element or tab 145 is part of a planar clip 142 formed in one piece out of a lubricated polycarbonate. Clip 142 has a C-shaped body 147, and tab 145 projects radially inward within the central opening 149 of body 147. Retention ears 152 jut in from body 147. Clip 142 is constrained to the plunger drive portion 160 that inserts through opening 149 by the inner face of tab 145 engaging plunger surface 162 and the ears 152 engaging plunger rail portions 164 and the inside diameter of body 147 engaging the sides of the drive portion 160. Plunger drive portion 160 is injection molded as a single piece from a thermoplastic material and includes sound elements 170. Sound elements 170 are formed as a series of transversely extending ribs axially spaced along the length of drive portion 160 within a channel 172. Ribs 170 are only provided on a single side of drive portion 160. Ribs 170 are square in axial cross section.

As shown in FIG. 9, audible injecting progress indicator 140 is used with a syringe carriage or holder 180. The carriage 180 may be used to move the syringe shown at 181 within a device housing. Syringe carriage 180 includes a rigid base formed of a C-shaped lower region 182, a top region 184 with a central aperture 185 through which drive portion 160 extends toward syringe plunger 194, and a spanning body 186. A strip 188 of resilient material, which may be molded to lower region 182, is provided on the top surface of lower region 182. Carriage 180 can be made from multiple component parts.

Clip 142 axially fits within the cavity 196 of carriage 180 directly between carriage top region 184 and syringe flange 190. Clip body 147 is sized and shaped to fit on syringe flange 190 such that tab 145 projects above the open interior of syringe barrel 198. The axial height and compressability of strip 188 serves to cushion the force at the end of the syringe insertion stroke.

During use, as plunger drive portion 160 moves through carriage 180 to advance syringe plunger 194 in syringe barrel 198, sound element ribs 170 engage with actuating element 145 as they pass through clip 142 to produce sounds indicating injecting progress. Specifically, as each rib 170 so passes, the rib engages tab 145 so as to bend the tab downward relative to clip body 147 and into the interior space ringed by syringe flange 190. When the engaged rib 170 passes below the inward tip of bent tab 145, the resiliency of clip 142 snaps the tab 145 upward so as to strike the underside 187 of carriage top region 184. This striking that results from the snap return produces a click, potentially amplified by the space within barrel 198 above the plunger 194 acting as a resonance chamber, which is audible to a user.

Figure 10:
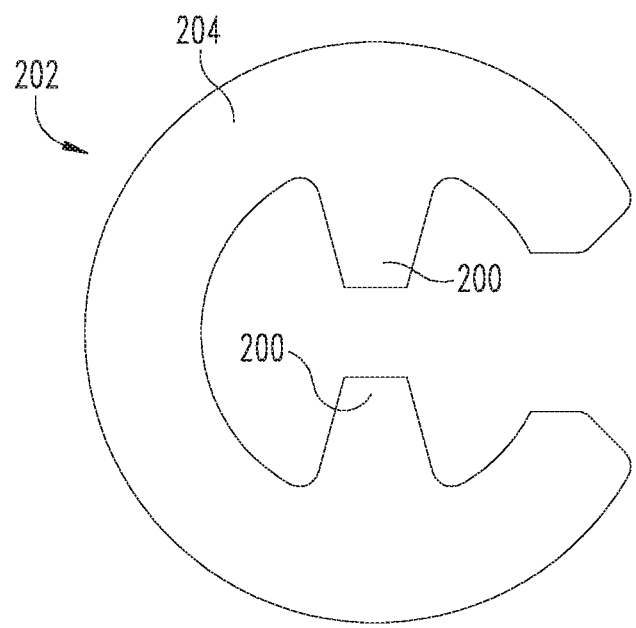
FIG. 10 is a top view of a clip with actuating elements for still another alternate audible indicator.
Figure 11:
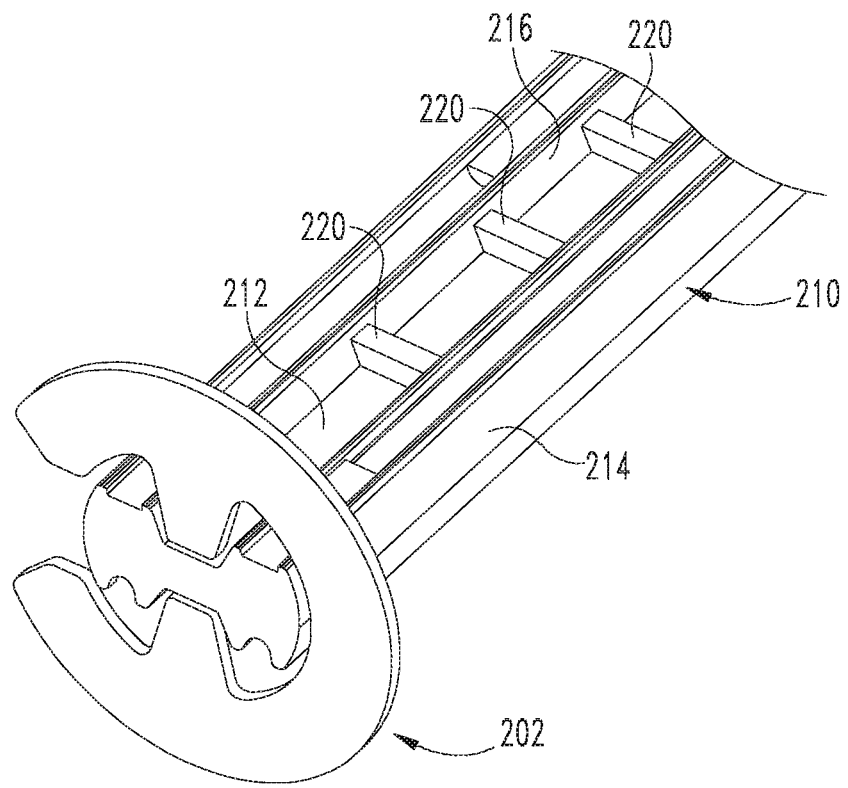
FIG. 11 is a perspective view of the clip of FIG. 10 mounted to another partially shown plunger element that includes sound elements.
Figure 12:
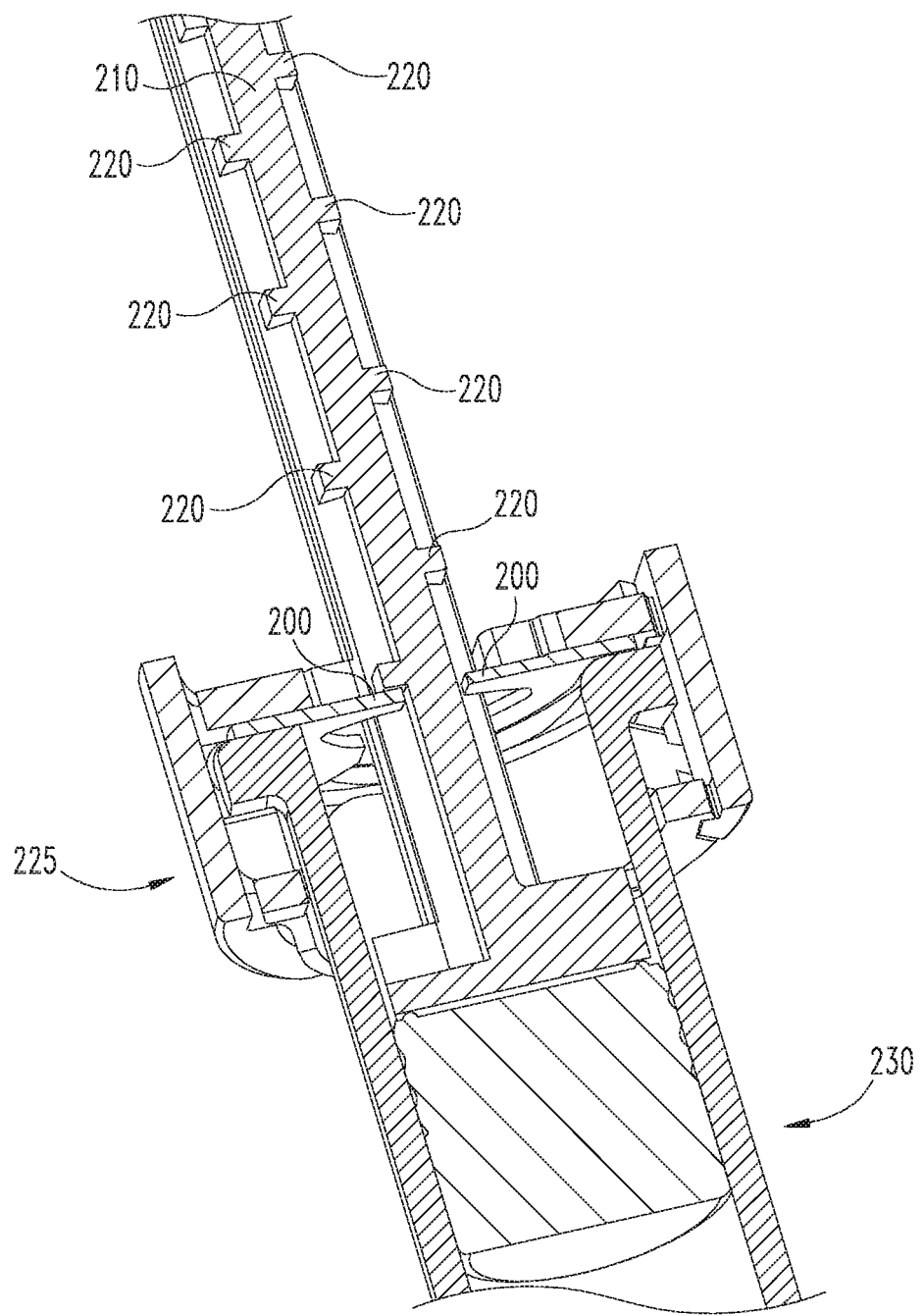
FIG. 12 is a perspective view in longitudinal cross-section of select portions of an automatic medication injection device which includes the actuating elements and sound elements of FIGS. 10 and 11.

Referring now to FIGS. 10-12, there is shown details of an alternate audible injecting progress indicator that is similar in many respects to the embodiment shown in FIGS. 7-9, and therefore differences are explained below. Two actuating elements or tabs 200 are provided on C-shaped body 204. Clip 202 is constrained to the plunger drive portion 210 by the inner faces of tabs 200 engaging plunger surface 212 and the inside diameter of body 204 engaging the side 214 of drive portion 210.

Sound elements 220 are formed as square shaped ribs on both sides of drive portion 210 within channels 216. The sound elements 220 are shown as alternating from side to side of the drive portion 210 in the axial direction. The axial positioning of the sound elements could be identical on both sides of the drive portion 210 in another embodiment.

The syringe carriage 225 and syringe 230 are identical to those shown in FIG. 9, and the actuating elements 200 and sound elements 220 work in an analogous fashion as their counterparts in the embodiment of FIGS. 7-9.

Figure 13:
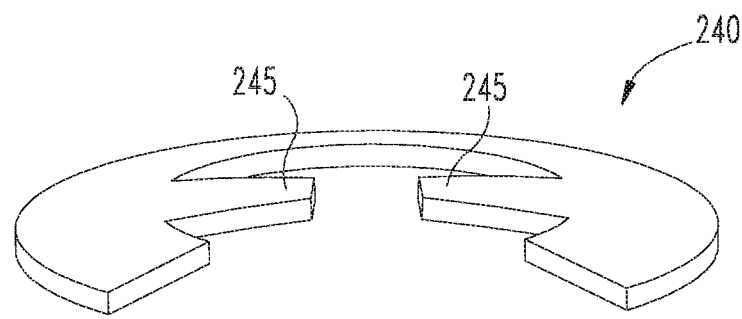
FIG. 13 is a top perspective view of an alternate clip with actuating elements.
Figure 14:
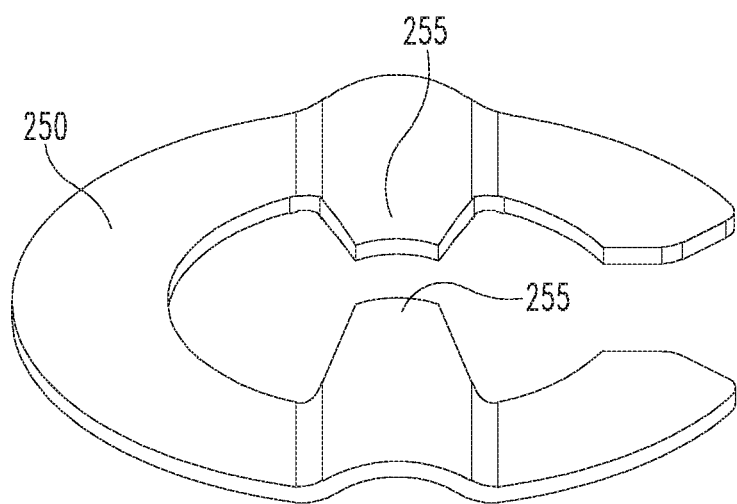
FIG. 14 is a top perspective view of still another alternate clip with actuating elements.

Although the clips with actuating elements shown in the embodiments of FIGS. 1-12 are each planar, other configurations may be used. For example, FIG. 13 shows a clip 240 with actuating tabs 245 that is entirely convex or dish-shaped. Similarly, FIG. 14 shows a clip in which the C-shaped body 250 is still planar, but the two actuating tabs 255 are curved to provide additional stiffness. These stiffer designs may provide for a louder click, or allow a thinner material to be used.

Figure 15:
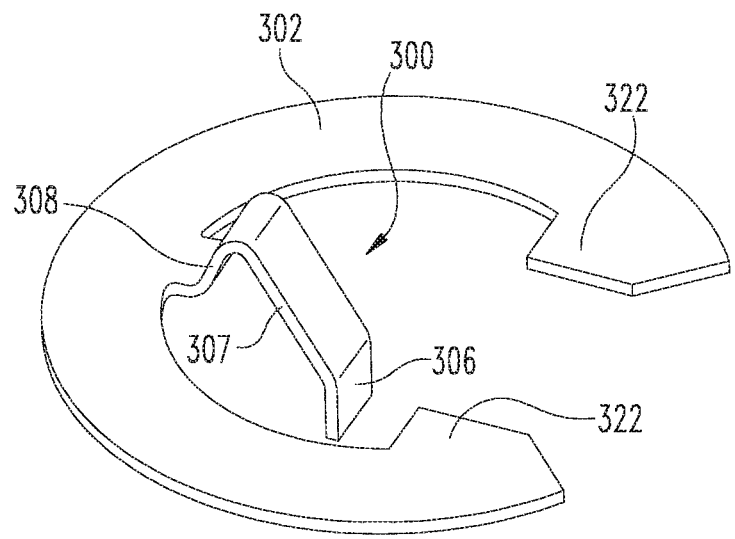
FIG. 15 is a top perspective view of a clip with actuating element for still another alternate audible indicator.
Figure 16:
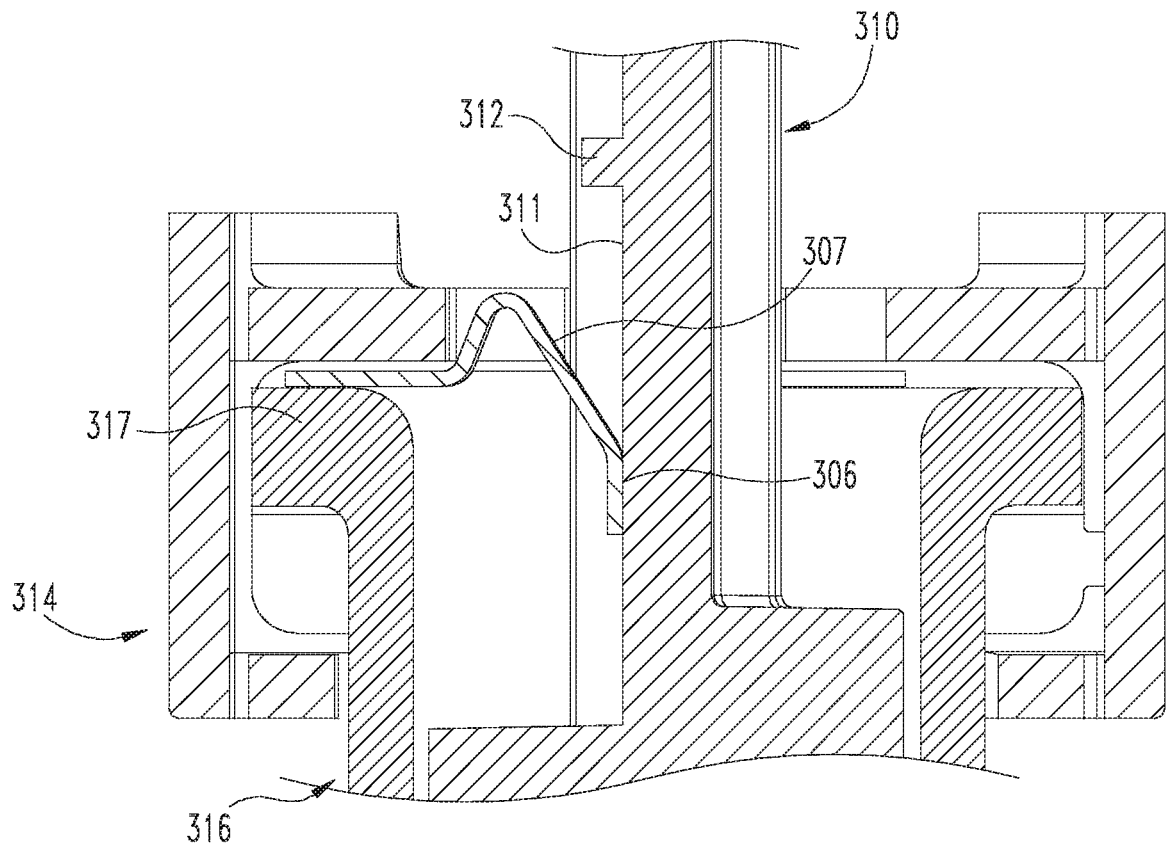
FIG. 16 is a front view in longitudinal cross-section of select portions of an automatic medication injection device which includes the actuating element of FIG. 15.

Referring now to FIGS. 15 and 16, there is shown details of still another alternate audible injecting progress indicator. The actuating element 300 is formed as a multi-angled extension that projects from a C-shaped body 302. The actuating element 300 and body 302 are stamped and formed integrally from sheet metal. The plunger drive portion 310 with sound element ribs 312, the syringe carriage 314, and the syringe 316 are identical to those corresponding components of the embodiment of FIGS. 7-9.

Actuating element 300 includes an inward end section 306 that is aligned axially and abuts plunger surface 311. An inclined section 307 extends from end section 306 and terminates at an oppositely inclined base section 308 that extends to body 302. Body 302 fits on syringe flange 317 and is axially captured between the syringe flange 317 and syringe carriage 314, but with an axial gap typically present due to part tolerances.

The body 302 includes ears 322 and is shaped the same as body 147 and ears 152 of the embodiment of FIG. 7.

During use, when plunger drive portion 310 advances the syringe plunger, each sound element rib 312 slidably engages inclined section 307 to bend it outward so as to allow the rib 312 to fit inward of end section 306. When the rib 312 passes beyond the lower tip of end section 306, the resiliency provided by the multi-angled design of actuating element 300 snaps the end section 306 inward into contact with the plunger surface 311 above the passed rib 312 to produce a click audible to a user.

Each of the embodiments shown in the Figures utilizes one or more actuating elements that are integrated into a clip that engages the plunger drive portion so as to locate the actuating element(s) for operation with the sound elements throughout operation. It will be appreciated that such locating need not be provided by a plunger engaging clip, as the locating function can be performed otherwise as needed, such as an engagement by the end of the actuating element which does not engage the plunger drive portion with other portions of the device, for example the syringe carriage.

Device 20 in general, including with the alternate audible injecting progress indicators described, and more particularly the technology claimed in this application, may be utilized in injecting a variety of medications or therapeutics into a person in need thereof. Syringes of the devices or claimed technology can be filled with any of a number of therapeutics, such as peptides, proteins, bi-functional proteins, antibodies, bi-functional protein-antibody, or bi-specific antibodies. For example, a syringe may be filled with a sclerostin antibody, such as blosozumab. For other examples, a syringe may be filled with a myostatin antibody, an Amyloid Beta antibody, a pegylated Amyloid Beta antibody fragment, a proprotein convertase subtilisin/kexin type 9 antibody, or a calcitonin gene-related peptide antibody. The device, or claimed technology of this application, may then be operated in a manner generally as described above with respect to device 20 to inject a person with such therapeutic in the syringe.

While this invention has been shown and described as having preferred designs, the present invention may be modified within the spirit and scope of this disclosure. For example, while device 20 provides an automatic needle insertion feature and thus the syringe needle does not project below the proximal end until the device is triggered, the instant audible injecting progress indicator could be used with an automatic injector in which the needle projects below a housing before use so as to be manually inserted into the user, after which a triggering automatically injects the medicine through the inserted needle. Furthermore, the device 20 could be adapted to have the drive mechanism advancement be stopped by user intervention, such as by redepressing the trigger button, and then restarted by an additional user triggering step to allow the injection to continue automatically. Still further, although the medication injection device 20 is shown as utilizing a container in the form of a syringe having a single outlet needle, the device could utilize different medication containers within the scope of the invention. Moreover, rather than a single needle, different alternative outlets from the container may be utilized within the scope of the invention as its teachings have applicability to other injection devices.

This application is therefore intended to cover any variations, uses or adaptations of the invention using its general principles. Further, this application is intended to cover such departures from the present disclosure as come within known or customary practice in the art to which this invention pertains.

We claim:

1. An automatic medication injection device comprising:
   a user grippable housing having a length extending in an axial direction between a proximal end and a distal end;
   a container of medication including an outlet that is disposed proximally of said housing proximal end at least during injection, said container including a barrel and a sealing plunger, said sealing plunger in sealing engagement with said barrel;
   a drive mechanism within said housing which when triggered automatically advances said container of medication within said housing and advances said sealing plunger proximally within said container to force medication from the outlet, said drive mechanism including an advancing portion that inserts within said barrel;
   a plurality of sound elements located on said advancing portion; and
   at least one actuating element movable axially within said housing with said container of medication, said at least one actuating element arranged to engage said plurality of sound elements to generate audible notices as said advancing portion moves past said at least one actuating element when advancing said sealing plunger for an injection, wherein said plurality of sound elements are axially spaced to provide a predetermined pattern of time intervals between said audible notices during the injection, a first time interval between said audible notices at the start of the injection being different than a second time interval between said audible notices at the end of the injection to indicate a nearing end of the injection.

2. The automatic medication injection device of claim 1 wherein said at least one actuating element extends from a body that seats on said container of medication.

3. The automatic medication injection device of claim 1 wherein said at least one actuating element extends from a body that seats on a holder of said container of medication.

4. The automatic medication injection device of claim 1 wherein said at least one actuating element comprises two actuating elements spaced to define a gap through which said advancing portion extends, said gap between said two actuating elements leading to an opening defined by a continuous spring beam having opposite angular ends from which extend said two actuating elements.

5. The automatic medication injection device of claim 1 wherein said plurality of sound elements are axially spaced along a same side of said advancing portion.

6. The automatic medication injection device of claim 1 wherein the audible notices increase in volume at the end of the injection.

7. The automatic medication injection device of claim 2 wherein said body is axially captured directly between said container of medication and a holder of said container of medication.

8. The automatic medication injection device of claim 5 wherein said spacing results in time intervals that decrease between at least a last three consecutive audible notices at the end of the injection.

9. An automatic medication injection device for delivering a single dose comprising:
   a user grippable housing having a length extending in an axial direction between a proximal end and a distal end;
   a container of medication including an outlet that is disposed proximally of said housing proximal end at least during injection;
   a drive mechanism within said housing which when triggered automatically advances to force medication from the outlet for a single injection;
   a plurality of sound elements within said housing;
   at least one actuating element within said housing;
   at least one of said at least one actuating element and said plurality of sound elements configured to travel within said housing when said drive mechanism advances to force medication from the outlet so that said plurality of sound elements and said at least one actuating element move relative to each other to have said at least one actuating element engage said plurality of sound elements to generate audible notices during the injection;
   wherein each of said plurality of sound elements other than a most distal sound element has a spacing in the axial direction from a proximally adjacent one of said sound elements; and
   wherein said spacings are selected to provide a pattern of shortening time intervals between said audible notices throughout at least a portion of time that said drive mechanism advances to force medication from the outlet,
   wherein the pattern of shortening time intervals comprises a first time interval between said audible notices at the start of the injection that is different than a second time interval between said audible notices at the end of the injection to indicate a nearing end of the injection.

10. The automatic medication injection device of claim 9 wherein said spacings selected to provide a pattern of shortening time intervals comprises spacings that define at least two consecutive time intervals.

11. The automatic medication injection device of claim 9 wherein said spacings selected to provide a pattern of shortening time intervals comprises spacings that define at least three consecutive time intervals.

12. The automatic medication injection device of claim 9 wherein said spacings selected to provide a pattern of shortening time intervals comprises spacings that define at least four consecutive time intervals.

13. The automatic medication injection device of claim 9 wherein the audible notices increase in volume as the drive mechanism completes advancing to force medication from the outlet.

14. The automatic medication injection device of claim 9 wherein said at least one actuating element is provided on a clip disposed distally of said container of medication and which is axially movable with said container of medication relative to said housing during use.

15. The automatic medication injection device of claim 9 wherein said at least one actuating element extends from a body that seats on said container of medication.

16. The automatic medication injection device of claim 9 wherein medication within said container comprises a myostatin antibody.

17. The automatic medication injection device of claim 9 wherein medication within said container comprises an Amyloid Beta antibody.

18. The automatic medication injection device of claim 9 wherein medication within said container comprises a pegylated Amyloid Beta antibody fragment.

19. The automatic medication injection device of claim 9 wherein medication within said container comprises a proprotein convertase subtilisin/kexin type 9 antibody.

20. The automatic medication injection device of claim 9 wherein medication within said container comprises a calcitonin gene-related peptide antibody.

21. The automatic medication injection device of claim 9 wherein medication within said container comprises a sclerostin antibody.

22. The automatic medication injection device of claim 10 wherein a last to occur time interval of said at least two consecutive time intervals is ended by an audible notice generated by engagement of said at least one actuator arm with said most distal sound element.

23. The automatic medication injection device of claim 13 wherein said sound elements are disposed on a drive mechanism member that moves past said at least one actuating element when advancing to force medication from the outlet.

24. The automatic medication injection device of claim 14 wherein said clip seats on a holder of said container of medication.

25. The automatic medication injection device of claim 14 wherein said at least one actuating element comprises two actuating elements spaced to define a gap, said gap between said two actuating elements leading to an opening in said clip defined by a continuous spring beam having opposite angular ends from which extend said two actuating elements.

26. The automatic medication injection device of claim 15 wherein said body is axially captured directly between said container of medication and a holder of said container of medication.

27. The automatic medication injection device of claim 21 wherein said sclerostin antibody is blosozumab.

28. The automatic medication injection device of claim 23 wherein said drive mechanism member inserts within a barrel of said container of medication.

29. The automatic medication injection device of claim 23 wherein said plurality of sound elements are provided on each of two opposite sides of said drive mechanism member.

30. The automatic medication injection device of claim 25 wherein said spring beam is arcuately shaped and formed in the same plane as, and integrally with, said two actuating elements.

* * * * *